United States Patent [19]
Martin

[11] 3,946,614
[45] Mar. 30, 1976

[54] MULTI-POSITION CONDITION SENSING DEVICE

[75] Inventor: Ronald L. Martin, Mt. Prospect, Ill.

[73] Assignee: Honeywell Inc., Minneapolis, Minn.

[22] Filed: Aug. 15, 1973

[21] Appl. No.: 388,680

[52] U.S. Cl. ............................. 73/363.5; 337/361
[51] Int. Cl. .......................................... G01k 5/68
[58] Field of Search .......... 73/363.5, , 363.7, 363.9; 337/360, 361, 374, 380; 236/87, 101 R

[56] References Cited
UNITED STATES PATENTS

| | | | |
|---|---|---|---|
| 2,564,222 | 8/1951 | Joesting | 73/363.5 X |
| 2,601,377 | 6/1952 | Ellis | 236/87 X |
| 2,611,855 | 9/1952 | Turner | 73/363.5 X |
| 3,044,295 | 7/1962 | Shivers | 73/363.5 X |
| 3,163,043 | 12/1964 | Snider | 73/363.5 |
| 3,595,475 | 7/1971 | Morton | 236/101 R |

Primary Examiner—Jerry W. Myracle
Assistant Examiner—Joseph W. Roskos
Attorney, Agent, or Firm—Trevor B. Joike; Henry L. Hanson

[57] ABSTRACT

A condition sensing device, for mounting on a support structure in one of at least two positions where, for example, the positions are at substantially right angles to one another, comprises a set point lever and cam arrangement profiled in a manner to properly adjust the set point of the device in any of the positions of the device even though the position of the lever and cam arrangement remains fixed with respect to the support structure. This operation is accomplished by allowing the lever and cam to assume one of at least two positions with respect to the device and by profiling the cam surface to give proper set point adjustment in any of its positions; that is, the cam will have a camming surface for each of its possible positions.

10 Claims, 8 Drawing Figures

MULTI-POSITION CONDITION SENSING DEVICE

BACKGROUND OF THE INVENTION

This invention relates to condition sensing devices such as thermostats and humidistats.

When mounting such devices, particularly in ducts, access to the set point control lever or dial as well as the set point indicia may be difficult to obtain. Because of space and/or wiring requirements, it may be necessary to mount the device in such a position where the set point lever or dial is difficult to reach or where the set point indicia is difficult to see.

This invention eliminates these difficulties by providing a condition sensing device which may assume one of at least two spatial positions or orientations while the set point control is maintained in a constant, fixed spatial position.

SUMMARY OF THE INVENTION

This operation is accomplished by providing a set point cam capable of assuming one of at least two positions with respect to the condition sensing device. The cam is profiled to have a camming surface for each of its positions with respect to the device to yield proper adjustment of the set point. Thus, for example, if it is desired to mount the device on a support such that the set point lever always points down, the condition sensing device may be mounted in any of its positions on the support structure and the profiled cam will still yield proper set point adjustment. Proper set point adjustment may be defined, as an example, as identical set point control; that is, the camming surfaces are the same for each position of the cam. The cam is held down by a spring which contains a detent for holding the set point control lever in its various positions but yet allows set point adjustment.

DETAILED DESCRIPTION

Figure 1:
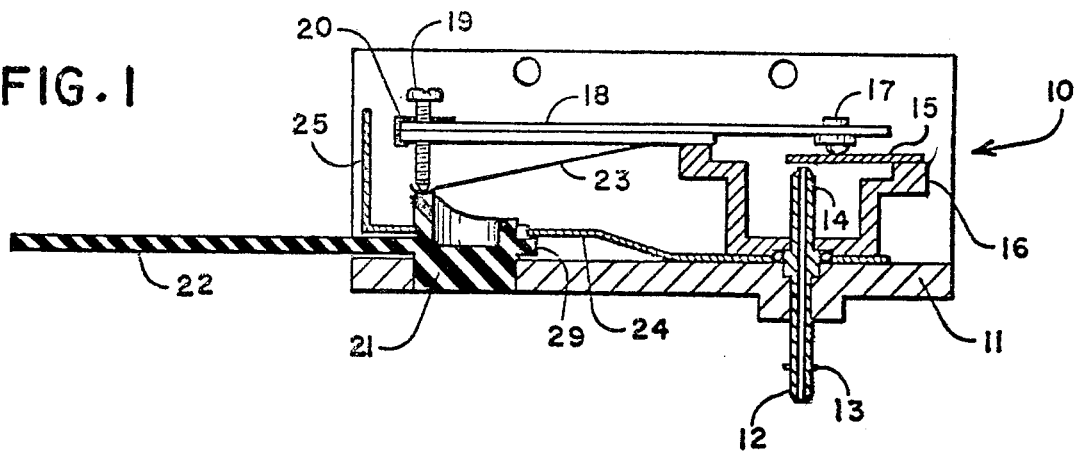
FIG. 1 is a cross sectional view of the condition sensing device.

A condition sensing device 10, in this case pneumatic, is shown in FIG. 1 and may be a thermostat or humidistat or other such condition sensing device. Supported on base assembly 11 is a connector tube 12 having a barb 13 therearound to grip the connecting hose (not shown). The tube 12 connects with the nozzle 14 co-acting with a flapper 15 supported by bracket 16. Bracket 16 is fixed to base 11 by suitable attaching means (not shown). The position of the flapper 15 with respect to nozzle 14 will determine the pneumatic pressure in tube 12. A throttling adjustment means 17 is mounted in a slot in the bi-metallic sensing element 18 for adjusting the throttling range of the sensing device. The bi-metallic element 18 is supported at one end, by suitable attaching means (not shown), by the bracket 16 and at the other end by a calibration screw 19 and a calibration screw retaining clip 20. A cam 21 is used as the set point control and is attached to a lever 22 for adjustment. The lower portion of cam 21 extends into a hole in the base 11 and cam 21 is held down to the base assembly 11 by a retaining spring 24 which also acts as support for the set point indicia.

A cam follower spring 23 rides on the cam surface of cam 21 and adjusts the position of the bi-metallic element 18 for controlling the set point of the sensing device. As the lever 22 is adjusted, the cam follower spring 23 will alter its position to in turn alter the position of the bimetallic element 18. The bi-metallic element 18 senses the condition, such as temperature, and will alter its position in response to the actual value of the condition sensed. the movement of the bi-metallic element 18 will control the position of the flapper 15 with respect to the nozzle 14.

Since it may be necessary to mount the condition sensing device 10 in at least two positions, for example vertically or horizontally, on a support structure, such as a duct, it is desirable to provide a set point cam and lever arrangement which may maintain a fixed position with respect to the support structure even though the device may assume at least two positions with respect to the support structure. Thus, provision is made in the supporting base 11 for the arm to extend either longitudinally or transversely of the device 10. That is, the set point lever 22 may extend longitudinally of the device 10 as shown in FIG. 5 or may be moved under the flanges 25 and 26 to a position transverse of the device 10 as shown in FIG. 6.

The set point lever can be adjusted in any of its positions to adjust the set point.

Figure 6:
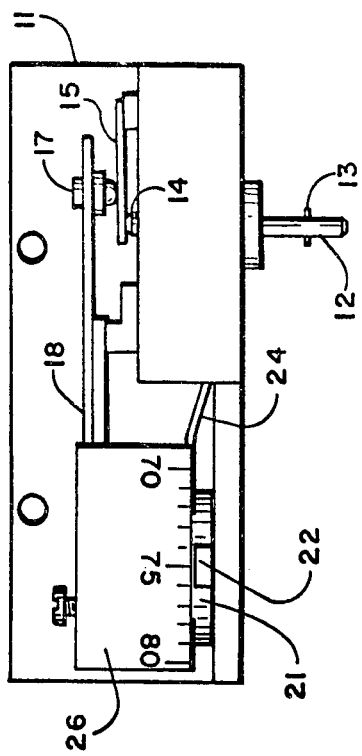
FIG. 6 is a side view of the condition sensing device.
Figure 5:
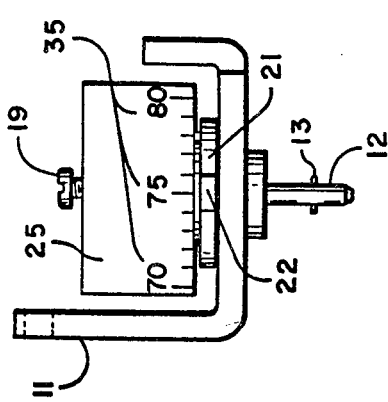
FIG. 5 is an end view of the condition sensing device.

Flange 25 of the spring 24 has provision for the mounting of indicia, FIG. 5, for the first position and flange 26 of the spring 24 has provision for the mounting of indicia, FIG. 6, for the second position of the second set point lever. A set point value indicator, such as a small projection (not shown), can be mounted on the lever 22 to indicate the value at which the set point lever has been set.

Figure 2:
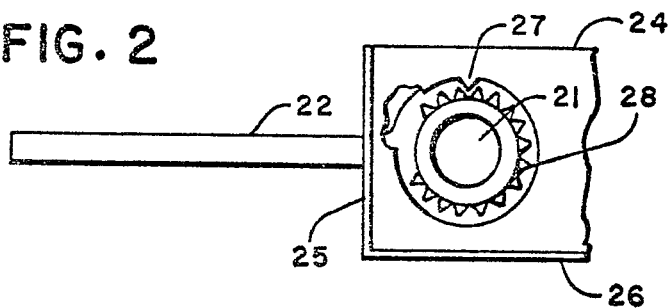
FIG. 2 shows a top view of a portion of the device shown in FIG. 1.
Figure 3:
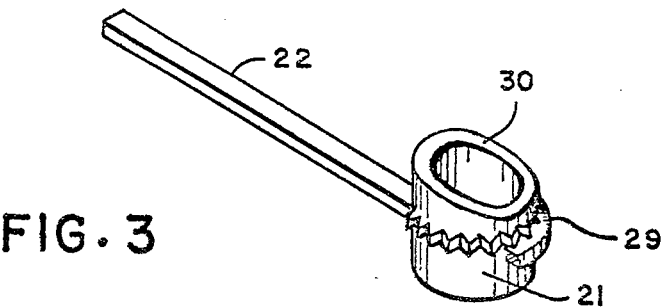
FIG. 3 is a pictorial view of the cam and set point lever.

In FIG. 2, spring 24 has a detent 27 designed to cooperate with the teeth 28 on the set point cam and lever arrangement. The detent 27 in cooperation with the teeth 28 will hold the cam in its chosen position. The cam profile is shown in FIG. 3 and has an enlarged portion 29 (shown in cut away in FIGS. 2 and 3) to allow the retention cam 21 and lever 22 by the hold down spring 24.

Figure 4:
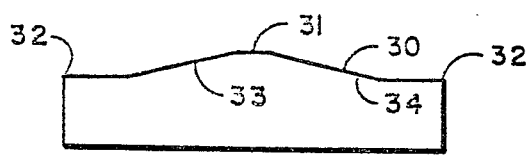
FIG. 4 is a development view of the cam surface profile.

FIG. 4 is a development view of the profile of the cam surface. The profile 30 is shown as having a peak 31 decreasing in both directions around the circumference of cam 21 to its lower position 32. Slope 33 of the profile is used for the set point control while the set point lever 22 is in, for example, its first position whereas the slope 34 of the cam profile is used while the cam lever is in its second position. Thus, the profile from peak 31 to low point 32 will be identical whether the lever extends longitudinally of the base member 11 or transversely of that base member. The set point control will be identical.

FIG. 5 shows an end view of the condition sensing device and particularly the indicia 35 on the flange 25 of the cam retaining spring 24. FIG. 6 shows a side view of the condition sensing device and particularly the flange 26 having the indicia mounted upside down thereon. The indicia on flange 26 is arranged in the manner shown so that when the condition sensing device is mounted in the duct, the indicia will read properly. Furthermore, the cam is profiled to provide proper set point control regardless of whether the indicia on flange 25 is used or the device is mounted such that the indicia on flange 36 is used.

Figure 8:
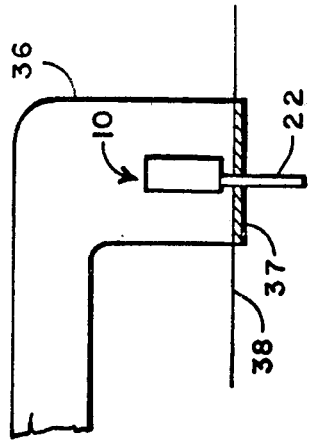
FIGS. 7 and 8 show the device mounted in a duct.
Figure 7:
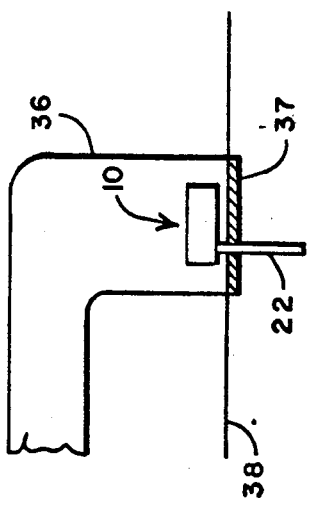

The device 10 may be used to adjust the dampers of a mixing box to control the percentages of outdoor air and return air being mixed dependent upon the temperature of the return air. In this case, device 10 is mounted above 38 in return air duct 26 (FIGS. 7 and 8) in such a position that the set point lever 22 protrudes through the return air grate or grid 37. FIG. 7 shows device 10 mounted in its horizontal position with lever 22 extending transversely of device 10. FIG. 8 shows device 10 mounted in its vertical position with lever 22 extending longitudinally of device 10.

There are, of course, modifications that can be made but yet will fall within the scope of the claims. As an example, the device 10 can be mounted on a wall or other structure as well as a duct. As another example, the set point can be provided by a dial as well as lever 22.

The embodiments of the invention in which an exclusive property or right is claimed are defined as follows:

1. A condition sensing device adapted for mounting on one of at least two orientations on a support structure, said device comprising:
   housing means;
   condition sensing means mounted within said housing means for sensing a condition;
   set point means for establishing a set point for said condition sensing means, said set point means being mountable in a first position having a first orientation with respect to said housing means and mountable in a second position having a second orientation with respect to said housing means and being adjustable about said first and second positions; and,
   output means responsive to said condition sensing means and set point means, for providing an output dependent upon the sensed condition and the set point.

2. The condition sensing device of claim 1 wherein said condition sensing means comprises a bi-metallic element.

3. The condition sensing device of claim 2 wherein said set point means comprises a cam profiled for proper set point adjustment in any of said positions of said set point means and a cam follower connected to said bi-metallic element.

4. The condition sensing device of claim 3 comprising a cam hold down spring having a flange supporting indicia for each of said positions of said set point means.

5. The condition sensing device of claim 4 wherein said spring is provided with a detent and the cam is provided with teeth to mesh with said detent.

6. The condition sensing device of claim 5 wherein said condition sensing means comprises a flapper and connecting means for translating the motion of said bi-metallic element to said flapper, said flapper cooperating with a nozzle means.

7. The condition sensing device of claim 6 wherein said set point means comprises a lever for adjusting said cam.

8. The condition sensing device of claim 11 wherein said set point means comprises a cam profiled for proper set point adjustment in any of said positions and a cam follower connected between said cam and said condition sensing means.

9. The condition sensing device of claim 8 wherein said condition sensing means comprises a bi-metallic element.

10. A condition sensing device adpated for mounting in one of at least two positions on a support structure, said device comprising:
    bi-metallic sensing means for sensing said condition;
    set point means comprising cam means for establishing a set point, said set point means being mountable in a first position having a first orientation with respect to said bi-metallic sensing means and mountable in a second position having a second orientation with respect to said bi-metallic sensing means, said cam means having a first profile for adjusting said set point in said first position and a second profile for adjusting said set point in said second position;
    cam follower means responsive to said cam profile and connected to said sensing means; and
    control means responsive to the position of said bi-metallic sensing means for providing an output dependent upon said sensed condition and said set point.

* * * * *

UNITED STATES PATENT OFFICE
CERTIFICATE OF CORRECTION

PATENT NO. : 3,946,614
DATED : April 8, 1976
INVENTOR(S) : RONALD L. MARTIN

It is certified that error appears in the above—identified patent and that said Letters Patent are hereby corrected as shown below:

Column 4, line 20, change -- 11 -- to "1".

Signed and Sealed this eighth Day of June 1976

[SEAL]

Attest:

RUTH C. MASON
*Attesting Officer*

C. MARSHALL DANN
*Commissioner of Patents and Trademarks*